(12) United States Patent
Assmann et al.

(10) Patent No.: US 7,008,593 B2
(45) Date of Patent: Mar. 7, 2006

(54) DEODORIZATION OF CATIONIC ACETONITRILE DERIVATIVES

(75) Inventors: Georg Assmann, Juechen (DE); Horst-Dieter Speckmann, Duesseldorf (DE); Wolfgang Lahn, Willich (DE); Michael Lusse, Krefeld (DE); Joerg Poethkow, Neuss (DE); Birgit Middelhauve, Monheim (DE); Gerhard Blasey, Duesseldorf (DE); Helga Werner, Rommerskirchen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 7 days.

(21) Appl. No.: 11/000,303

(22) Filed: Nov. 30, 2004

(65) Prior Publication Data

US 2005/0079988 A1     Apr. 14, 2005

Related U.S. Application Data

(63) Continuation of application No. PCT/EP03/05346, filed on May 22, 2003.

(30) Foreign Application Priority Data

May 31, 2002  (DE) ................................ 102 24 509
Oct. 28, 2002  (DE) ................................ 102 50 254

(51) Int. Cl.
*A61L 2/18*     (2006.01)
*C11D 1/62*    (2006.01)
*C11D 3/30*    (2006.01)

(52) U.S. Cl. ................... 422/28; 510/303; 510/314; 510/376; 510/382; 510/383; 510/477; 510/488; 510/504

(58) Field of Classification Search .............. 510/303, 510/314, 376, 382, 383, 477, 488, 504; 422/28
See application file for complete search history.

(56) References Cited

U.S. PATENT DOCUMENTS

| | | | |
|---|---|---|---|
| 3,122,417 A | 2/1964 | Blaser et al. | |
| 5,114,434 A | 5/1992 | Praulus et al. | |
| 6,063,750 A | 5/2000 | Löffler et al. | |
| 6,183,708 B1 | 2/2001 | Hei et al. | |
| 2002/0107163 A1 * | 8/2002 | Borchers et al. | ............ 510/302 |
| 2003/0166484 A1 | 9/2003 | Kingma et al. | |
| 2004/0059148 A1 | 3/2004 | Schrieber et al. | |
| 2004/0067862 A1 | 4/2004 | Speckmann et al. | |
| 2004/0067863 A1 | 4/2004 | Speckmann et al. | |

FOREIGN PATENT DOCUMENTS

| | | |
|---|---|---|
| CA | 2 304 033 | 3/1999 |
| DE | 11 07 207 | 5/1961 |
| DE | 198 29 159 A1 | 1/1998 |
| DE | 197 40 669 A1 | 3/1999 |
| DE | 197 40 671 A1 | 3/1999 |
| DE | 100 38 086 A1 | 2/2002 |
| DE | 100 38 845 A1 | 2/2002 |
| DE | 100 38 832 A1 | 3/2002 |
| DE | 100 49 237 A1 | 4/2002 |
| EP | 0 365 585 | 3/1990 |
| EP | 0 464 880 A1 | 1/1992 |
| WO | WO 96/40661 A1 | 12/1996 |
| WO | WO 02/12175 A2 | 2/2002 |

OTHER PUBLICATIONS

David B. Luten et al., "The Preparation of Aminonitriles and their quaternary ammonium derivatives", *Journal of Organic Chemistry*, American Chemical Society, Easton, US, Nr. 3, pp. 588-597, XP002245667, ISSN:0022-3263, Table II (1938).

* cited by examiner

*Primary Examiner*—Gregory R. Del Cotto
(74) *Attorney, Agent, or Firm*—Glenn E. J. Murphy

(57) ABSTRACT

A process of deodorizing water-containing solutions of cationic nitrile bleach activators by exposure to the action of a combination of a percarboxylic acid, a carboxylic acid and hydrogen peroxide.

13 Claims, No Drawings

US 7,008,593 B2

DEODORIZATION OF CATIONIC ACETONITRILE DERIVATIVES

CROSS REFERENCE TO RELATED APPLICATION

This application is a continuation under 35 U.S.C. § 365(c) and 35 U.S.C. § 120 of international application PCT/EP03/05346, filed on May 22, 2003. This application also claims priority under 35 U.S.C. § 119 of DE 102 24 509.6, filed May 31, 2002 and DE 102 50 254.4, filed Oct. 28, 2002, each of which is incorporated herein by reference in its entirety.

BACKGROUND OF THE INVENTION

The present invention relates to a process for deodorizing certain cationic nitrile bleach activators.

European patent application EP 0 464 880 discloses cationic nitrites of the general formula R'R''R'''N$^+$—CR$_1$R$_2$—CN X$^-$, where R$_1$ and R$_2$ are hydrogen or a substituent having at least one carbon atom, R' is a C$_{1-24}$-alkyl, alkenyl or alkyl ether group or a group —CR$_1$R$_2$—CN, and R'' and R''' are each individually a C$_{1-24}$-alkyl or hydroxyalkyl group and the counterion X$^-$ is an organic sulfonate, an organic sulfate or a carboxylate. These compounds are useful as bleach activators in laundry detergents. They act as bleach activators in the sense that they react with hydrogen peroxide present to form a perimidic acid that has a stronger bleach activity than the hydrogen peroxide.

Compounds of this type are usually prepared by reacting aldehydes or ketones (depending on the radicals R$_1$ and R$_2$) with a secondary amine (in which case the radicals R'' and R''' are bound to the nitrogen atom) and an alkyl metal cyanide. The resultant aminonitrile is then quaternized on the nitrogen atom of the amino group by reaction with an alkylating agent or an alkenylating agent (depending on the radical R'), for example dimethylsulfate, generally, the counterion X$^-$ also resulting from the alkylating agent. If desired, this counterion, which is usually chloride, sulfate, hydrogensulfate or methylsulfate, can then be exchanged by solvent ion exchange for another counterion, for example a carboxylate, benzenesulfonate or longer-chain alkylsulfate, as a result of which, as is known, the stability of the compound can be increased. Said patent application EP 0 464 880 proposes carrying out the anion exchange in methanolic or isopropanolic solution. The international patent application WO 02/12175 discloses that the exchange of anions can also be carried out in the presence of water at elevated temperature.

As a result, the target compound, the cationic nitrile, is present in water or, if appropriate, organic solvent, and can be used in this form for bleach-activating purposes. Advantageously, however, in particular for use in particulate laundry compositions or cleaning compositions, it is converted in advance into an additionally more storage-stable particulate form that, in its simplest form, can be achieved by removing the solvent, but usually includes a granulation step and/or encapsulation step. The production of granules having a bleach-activating cationic nitrile and, if appropriate, support material, and/or an encapsulation layer, is disclosed, for example, by the German patent applications DE 197 40 669, DE 197 40 671, DE 100 38 086, DE 100 38 823, DE 100 38 845, or DE 100 49 237.

After preparing the target compound, it can be advantageous to improve the odor of solutions or particles which comprise the active substance. Possible causes of odor are, for example, starting materials used in synthesis that remain as impurities, as well as the target compound itself.

The present invention is intended to provide a remedy by means of a treatment step which reliably prevents the occurrence of odor, or at least reduces this below the threshold of perception.

Customary processes for removing volatile components, for example steam distillation under, if appropriate, reduced pressure, do not lead to success on their own, or require an unacceptably long time.

Surprisingly, it has been found that deodorization is simply and reliably possible by using certain oxidizing agents.

DESCRIPTION OF THE INVENTION

The invention relates to a process of deodorizing water-containing solutions of compounds of the general formula I,

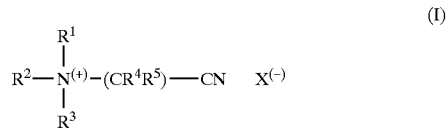

(I)

$$R^2-\overset{R^1}{\underset{R^3}{N^{(+)}}}-(CR^4R^5)-CN \quad X^{(-)}$$

where R$^1$ is H, CH$_3$, a C$_{2-24}$-alkyl or alkenyl radical, a substituted C$_{2-24}$-alkyl or -alkenyl radical having at least one substituent from the group consisting of Cl, Br, OH, NH$_2$, CN, an alkyl radical or an alkenylaryl radical having a C$_{1-24}$-alkyl group, or a substituted alkyl or alkenylaryl radical having a C$_{1-24}$-alkyl group and at least one further substituent on the aromatic ring, R$^2$ and R$^3$ independently of one another are selected from —CH$_2$—CN, —CH$_3$, —CH$_2$—CH$_3$, —CH$_2$—CH$_2$—CH$_3$, —CH(CH$_3$)—CH$_3$, —CH$_2$—OH, —CH$_2$—CH$_2$—OH, —CH(OH)—CH$_3$, —CH$_2$—CH$_2$—CH$_2$—OH, —CH$_2$—CH(OH)—CH$_3$, —CH(OH)—CH$_2$—CH$_3$, —(CH$_2$—CH$_2$—O)$_n$H where n=1, 2, 3, 4, 5 or 6, R$^4$ and R$^5$ independently of one another have a meaning specified above for R$^1$, R$^2$ or R$^3$, and X is an anion of equivalent charge, by exposure to the action of a combination of a percarboxylic acid, a carboxylic acid and hydrogen peroxide.

Said combination is preferably used in aqueous solution which usually comprises from 30% by weight to 80% by weight of water, but if desired can also be more concentrated or more diluent.

Preferred percarboxylic acids are performic acid, peracetic acid, perpropionic acid, perbenzoic acid and/or substituted derivatives thereof, for example m-chloroperbenzoic acid. The preferred carboxylic acids comprise formic acid, acetic acid, propionic acid, benzoic acid, fumaric acid, maleic acid and/or adipic acid, in the case of these, substituted derivatives thereof also being able to be used. It is further preferred if, in the combination, the percarboxylic acid corresponding to the carboxylic acid used is present, for example the combination of formic acid and performic acid, or the combination of acetic acid and peracetic acid. Deodorizing combinations of this type can be prepared in a simple manner by mixing aqueous hydrogen peroxide solution, preferably having a concentration from about 30% by weight to about 70% by weight, with the desired carboxylic acid, which can be in aqueous solution, preferably having a concentration greater than 50% by weight, or anhydrous, if appropriate with addition of a stabilizer. Instead of the carboxylic acid, if desired, derivatives, for example anhydrides or acid chlorides, can also be used. The ratio of carboxylic acid to hydrogen peroxide can be varied within broad limits with the proviso that the proportion of free hydrogen peroxide in the solution intended for use is as low as possible. Preference is given to solutions having a weight ratio of carboxylic acid to hydrogen peroxide of from about 8:1 to about 30:1, or from about 0.5:1 to about 1:1, based on anhydrous content. Percarboxylic acid forms from the carboxylic acid and hydrogen peroxide in accordance with the equation $R\text{—}CO_2H+H_2O_2 \rightarrow R\text{—}CO_3H+H_2O$. The mixtures which are made up are preferably not used directly, but stored in advance, so that a percarboxylic acid and carboxylic acid content corresponding to the equilibrium according to the given reaction equation and its back reaction can be established (what is termed "equilibrium peracid"). The formation of the percarboxylic acid can, if desired, be accelerated catalytically by adding a small amount (for example 0.1% by weight up to 1% by weight, based on the aqueous mixture) of a mineral acid, for example sulfuric acid. By adding water, it is possible to vary in the simplest manner the concentration of carboxylic acid and, in the context of the described equilibrium reaction, also the concentration of percarboxylic acid in solution.

The inventive process preferably uses aqueous deodorizing combinations, the concentrations of which of carboxylic acid are from about 15% by weight to 60% by weight, in particular from about 15% by weight to 30% by weight, or from about 40% by weight to 60% by weight, percarboxylic acid of from about 3% by weight to 10% by weight, in particular from 2% by weight to 5% by weight, and/or of hydrogen peroxide up to 30% by weight, in particular from 0.1% by weight to 25% by weight, particularly preferably from about 0.5% by weight to 3% by weight, in each case based on anhydrous content. In addition to water and said small optional mineral acid content due to production, the deodorization combination can if desired comprise stabilizers, that is to say in particular compounds which are able to bind the heavy metal ions in a complex manner and inhibit the decomposition of the peroxygen compounds. Preferably, phosphonic acids or polyphosphonic acids are used for this. Complexing agents of this type are, for example, dimethylaminomethanediphosphonic acid, 3-aminopropane-1-hydroxy-1,1-diphosphonic acid, 1-amino-1-phenylmethanediphosphonic acid, 1-hydroxyethane-1,1-diphosphonic acid, aminotris(methylenephosphonic acid), N,N,N',N'-ethylenediamine-tetrakis(methylenephosphonic acid) and the acylated derivatives of phosphoric acid described in German laid-open application DE 11 07 207. The content of stabilizers in the deodorization combination solutions of the inventive process is usually not above 3% by weight, preferably the range is from 0.01% by to 2% by weight.

The inventive deodorization process is preferably carried out at room temperature or at temperatures slightly above, for example up to 30° C. As a result of the heat of reaction, the temperature can also reach over 60° C. The deodorization combination usually acts until the active compounds present in it have reacted to exhaustion or have decomposed, that is to say it is generally not removed again from the solution of the cationic nitrile.

An indication for the ratios required can be the fact that an amount of from 1 part by weight to 2 parts by weight of a 50% strength by weight water-containing equilibrium percarboxylic acid is usually completely sufficient for satisfactory deodorization of 100 parts by weight of the same concentration of aqueous solution of the cationic nitrile. If the solution of the cationic nitrile to be deodorized does not already have, due to production, an acidic pH in the range of, preferably, pH 3 to pH 5, it can be set to corresponding values by adding system-compatible acids, for example sulfuric acid.

Those skilled in the art can, if desired, employ customary process steps for removing readily volatile substances, for example said steam distillation, in addition to the inventive deodorization process, without problem, these process steps being able to follow or precede the inventive process.

The inventive deodorization process is preferably employed on compounds according to formula I, where $R^1$, $R^2$ and $R^3$ are identical. Among these, those compounds are preferred where said radicals are methyl groups. Secondly, those compounds are preferred where at least one or two of said radicals are methyl groups and the others have a plurality of carbon atoms. The anions $X^-$ of the compounds according to formula I comprise, in particular, the halides, such as chloride, fluoride, iodide and bromide, nitrate, hydroxide, phosphate, hydrogenphosphate, dihydrogenphosphate, pyrophosphate, metaphosphate, hexafluorophosphate, carbonate, hydrogencarbonate, sulfate, hydrogensulfate, $C_{1-20}$-alkyl sulfate, $C_{1-20}$-alkyl sulfonate, unsubstituted or $C_{1-18}$-alkyl substituted arylsulfonate, chlorate, perchlorate and/or the anions of $C_{1-24}$-carboxylic acids, such as formate, acetate, laurate, benzoate or citrate, alone or in any mixtures. Preference is given to compounds according to formula I where $X^-$ is chloride, sulfate, hydrogensulfate, ethosulfate, $C_{12/18}$-, $C_{12/16}$- or $C_{13/15}$-alkyl sulfate, lauryl sulfate, dodecylbenzenesulfonate, toluenesulfonate, cumenesulfonate, xylenesulfonate or methosulfate, or mixtures of these. Toluenesulfonate, or cumenesulfonate, are taken to mean here the anion of the ortho-, meta- or para-isomers of methylbenzenesulfonic acid, or isopropylbenzenesulfonic acid and any mixtures of these. Para-isopropylbenzenesulfonic acid is particularly preferred.

Following on the inventive deodorization process, the cationic nitrile according to formula I can be further processed, in principle in a known manner, to give powders, compacted materials, or granules. The bleach-activating action of the acetonitrile derivative according to formula I is not adversely affected in any manner by the inventive deodorization process.

An acetonitrile derivative according to formula I which has been deodorized by the inventive process is used in laundry detergents or cleaning compositions, preferably in amounts of from 0.5% by weight to 10% by weight, in particular from 1% by weight to 7% by weight.

As used herein, and in particular as used herein to define the elements of the claims that follow, the articles "a" and "an" are synonymous and used interchangeably with "at least one" or "one or more," disclosing or encompassing both the singular and the plural, unless specifically defined otherwise. The conjunction "or" is used herein in its inclusive disjunctive sense, such that phrases formed by terms conjoined by "or" disclose or encompass each term alone as well as any combination of terms so conjoined, unless specifically defined otherwise. All numerical quantities are understood to be modified by the word "about," unless specifically modified otherwise or unless an exact amount is needed to define the invention over the prior art.

What is claimed is:

1. A process of deodorizing water-containing solutions of compounds of the general formula I,

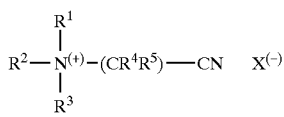

where $R^1$ is H, $CH_3$, a $C_{2-24}$-alkyl or alkenyl radical, a substituted $C_{2-24}$-alkyl or -alkenyl radical having at least one substituent from the group consisting of Cl, Br, OH, $NH_2$, CN, an alkyl radical or an alkenylaryl radical having a $C_{1-24}$-alkyl group, or a substituted alkyl or alkenylaryl radical having a $C_{1-24}$-alkyl group and at least one further substituent on the aromatic ring, $R^2$ and $R^3$ independently of one another are selected from $-CH_2-CN$, $-CH_3$, $-CH_2-CH_3$, $-CH_2-CH_2-CH_3$, $-CH(CH_3)-CH_3$, $-CH_2-OH$, $-CH_2-CH_2-OH$, $-CH(OH)-CH_3$, $-CH_2-CH_2-CH_2-OH$, $-CH_2-CH(OH)-CH_3$, $-CH(OH)-CH_2-CH_3$, $-(CH_2-CH_2-O)_nH$ where n=1, 2, 3, 4, 5 or 6, $R^4$ and $R^5$ independently of one another have a meaning specified above for $R^1$, $R^2$ or $R^3$, and X is an anion of equivalent charge, by exposure to the action of an aqueous combination of a percarboxylic acid, a carboxylic acid and hydrogen peroxide, wherein the aqueous combination comprises 30% to 80% by weight of water.

2. The process of claim 1, wherein the percarboxylic acid is performic acid, peracetic acid, perpropionic acid, perbenzoic acid, or any mixture or substituted derivative of these.

3. The process of claim 1, wherein the carboxylic acid is formic acid, acetic acid, propionic acid, benzoic acid, fumaric acid, maleic acid, adipic acid, or any mixture thereof.

4. The process of claim 1, wherein, in the combination, the percarboxylic acid corresponding to the carboxylic acid used is present.

5. A process of the deodorizing water-containing solutions of compounds of the general formula I,

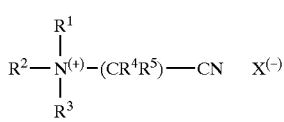

where $R^1$ is H, $CH_3$, a $C_{2-24}$-alkyl or alkenyl radical, a substituted $C_{2-24}$-alkyl or -alkenyl radical having at least one substituent from the group consisting of Cl, Br, OH, $NH_2$, CN, an alkyl radical or an alkenylaryl radical having a $C_{1-24}$-alkyl group, or a substituted alkyl or alkenylaryl radical having a $C_{1-24}$-alkyl group and at least one further substituent on the aromatic ring, $R^2$ and $R^3$ independently of one another are selected from $-CH_2-CN$, $-CH_3$, $-CH_2-CH_3$, $-CH_2-CH_2-CH_3$, $-CH(CH_3)-CH_3$, $-CH_2-OH$, $-CH_2-CH_2-OH$, $-CH(OH)-CH_3$, $-CH_2-CH_2-CH_2-OH$, $-CH_2-CH(OH)-CH_3$, $-CH(OH)-CH_2-CH_3$, $-(CH_2-CH_2-O)_nH$ where n=1, 2, 3, 4, 5 or 6, $R^4$ and $R^5$ independently of one another have a meaning specified above for $R^1$, $R^2$ or $R^3$, and X is an anion of equivalent charge, by exposure to the action of an aqueous combination of a percarboxylic acid, a carroxylic acid and hydrogen peroxide, wherein the aqueous deodorizing combination flas a carboxylic acid concentration of from 15% by weight to 60% by weight.

6. The process of claim 4, wherein the aqueous deodorizing combination has a percarboxylic acid concentration of from 3% by weight to 10% by weight.

7. The process of claim 4, wherein the aqueous deodorizing combination has a percarboxylic acid concentration of from 2% by weight to 5% by weight.

8. The process of claim 5, wherein the aqueous deodorizing combination has a hydrogen peroxide concentration up to 30% by weight.

9. The process of claim 8, wherein the aqueous deodorizing combination has a hydrogen peroxide concentration of from 0.1% by weight to 25% by weight.

10. The process of claim 1, wherein, in the compound according to formula I, the radicals $R^1$, $R^2$ and $R^3$ are identical.

11. The process of claim 1, wherein, in the compound according to formula I, the anion $X^-$ is selected from the group consisting of chloride, fluoride, iodide and bromide, nitrate, hydroxide, phosphate, hydrogenphosphate dihydrogenphosphate, pyrophosphate, metaphosphate, hexafluorophosphate, carbonate, hydrogencarbonate, sulfate, hydrogensulfate, $C_{1-20}$-alkylsulfate, $C_{1-20}$-alkylsulfonate, substituted or unsubstituted $C_{1-18}$-alkyl substituted arylsulfonate, chlorate, perchlorate and/or the anions of $C_{1-24}$-carboxylic acids such as formate, acetate, laurate, benzoate or citrate, alone or in any desired mixtures.

12. The process of claim 5, wherein, in the compound according to formula I, the radicals at $R^1$, $R^2$ and $R^3$ are identical.

13. The process of claim 5, wherein, in the compound according to formula I, the anion $X^-$ is selected from the group consisting of chloride, fluoride, iodide and bromide, nitrate, hydroxide, phosphate, hydrogenphosphate dihydrogenphosphate, pyrophosphate, metaphosphate, hexafluorophosphate, carbonate, hydrogencarbonate. sulfate, hydrogensulfate, $C_{1-20}$-alkylsulfate, $C_{1-20}$-alkylsulfonate, substituted or unsubstituted $C_{1-18}$-alkyl substituted arylsulfonate, chlorate, perchlorate and/or the anions of $C_{1-24}$-carboxylic acids such as formate, acetate, laurate, benzoate or citrate, alone or in any desired mixtures.

* * * * *